(12) United States Patent
Azar

(10) Patent No.: US 7,753,952 B2
(45) Date of Patent: Jul. 13, 2010

(54) VISION PROSTHESIS ORIENTATION

(75) Inventor: Dimitri T. Azar, Chicago, IL (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 71 days.

(21) Appl. No.: 12/140,678

(22) Filed: Jun. 17, 2008

(65) Prior Publication Data

US 2008/0249621 A1 Oct. 9, 2008

Related U.S. Application Data

(63) Continuation of application No. 10/847,515, filed on May 17, 2004, now Pat. No. 7,402,175.

(51) Int. Cl.
*A61F 2/14* (2006.01)
*G02C 7/04* (2006.01)

(52) U.S. Cl. ............. 623/5.14; 623/4.1; 623/5.11; 351/160 R

(58) Field of Classification Search ............ None
See application file for complete search history.

(56) References Cited

U.S. PATENT DOCUMENTS

| | | | |
|---|---|---|---|
| 2,241,415 A | 5/1941 | Moulton | |
| 3,962,505 A | 6/1976 | Avery | |
| 4,190,330 A | 2/1980 | Berreman | |
| 4,230,942 A | 10/1980 | Stauffer | |
| 4,298,996 A | 11/1981 | Barnet | |
| 4,309,603 A | 1/1982 | Stauffer | |
| 4,466,703 A | 8/1984 | Nishimoto | |
| 4,601,545 A | 7/1986 | Kern | |
| 4,728,182 A | 3/1988 | Kelman | |
| 4,787,903 A | 11/1988 | Grendahl | |
| 5,182,585 A | 1/1993 | Stoner | |
| 5,300,118 A | 4/1994 | Silvestrini et al. | |
| 5,359,444 A | 10/1994 | Piosenka et al. | |
| 5,593,437 A | 1/1997 | Arita et al. | |
| 5,800,530 A | 9/1998 | Rizzo, III | |
| 5,935,155 A | 8/1999 | Humayun et al. | |
| 6,187,041 B1 | 2/2001 | Garonzik | |
| 6,638,304 B2 | 10/2003 | Azar | |
| 2004/0054407 A1 | 3/2004 | Tashiro et al. | |

OTHER PUBLICATIONS

Gich et al., High-coercivity ultralight transparent magnets, Applied Physical Letters, vol. 82, No. 24, p. 4307-4309, (Jun. 13, 2003).
International Search Report, Patent Cooperation Treaty, International Application No. PCT/US05/17331, Sep. 19, 2006, 8 pages.

*Primary Examiner*—David H Willse
*Assistant Examiner*—Javier G Blanco
(74) *Attorney, Agent, or Firm*—Fish & Richardson P.C.

(57) ABSTRACT

A vision prosthesis includes an optical element having a surface that is shaped to be positioned near a cornea of an eye, and a magnetic element embedded in the optical element.

16 Claims, 7 Drawing Sheets

VISION PROSTHESIS ORIENTATION

CROSS-REFERENCE TO RELATED APPLICATIONS

This application is a continuation application of and claims priority to U.S. application Ser. No. 10/847,515, filed on May 17, 2004, now U.S. Pat. No. 7,402,175, incorporated herein by reference.

FIELD OF INVENTION

The invention relates to vision prosthesis orientation.

BACKGROUND

Loss of visual acuity from refractive errors in a person's vision can be caused by conditions such as hyperopia and myopia. Some restoration of visual acuity can be provided by spectacles or contact lenses. Loss of visual acuity can also be caused by wavefront aberrations due to irregularities in the eye (e.g., in the cornea or in the natural crystalline lens). The lenses in spectacles, unlike contact lenses, have a stable orientation with respect to the eye, and can therefore be used to correct asymmetric wavefront aberration. Some "toric contact lenses" are ballasted to reduce rotation in the eye. Some irregularities in the cornea such as astigmatism can be partially corrected by a hard contact lens that conforms the cornea to the shape of the lens.

SUMMARY

In one aspect, the invention features a vision prosthesis including an optical element having a surface that is shaped to be positioned near a cornea of an eye, and a magnetic element embedded in the optical element.

In some embodiments, the magnetic element includes magnetic particles embedded in the optical element.

In some embodiments, the magnetic element includes a first magnet at a first location on the optical element, the first location being selected to avoid intersection of the first magnet with a visual axis of the eye.

In some embodiments, the vision prosthesis includes a second magnet in the eye, the second magnet being disposed such that when the optical element is located over the cornea the second magnet is aligned with the first magnet.

In some embodiments, the vision prosthesis includes a second magnet at a second location on the optical element, the second location being selected to avoid intersection of the second magnet with a visual axis of the eye.

In some embodiments, the vision prosthesis includes third and fourth magnets in the eye, the third and fourth magnets being disposed such that when the optical element is located over the cornea and the third magnet is aligned with the first magnet, the second magnet is aligned with the fourth magnet.

In some embodiments, the second magnet is at an asymmetric location with respect to the first magnet.

In some embodiments, the third magnet is at a location in the eye including within the conjunctiva of the eye, under the conjunctiva of the eye, within the cornea of the eye, or under the cornea of the eye.

In some embodiments, the first and third magnets have different sizes.

In some embodiments, the third magnet is larger than the first magnet.

In some embodiments, the first magnet includes a ferromagnetic material or an electromagnet.

In some embodiments, the third magnet includes a ferromagnetic material or an electromagnet.

In some embodiments, the optical element includes a contact lens.

In some embodiments, the contact lens includes a hard contact lens.

In some embodiments, the contact lens includes a soft contact lens.

In some embodiments, the contact lens has a surface having an asymmetric shape.

In some embodiments, the vision prosthesis includes a portion of an imaging system attached to the optical element.

In some embodiments, the optical element includes an optical medium having a characteristic function associated with refraction therethrough, the characteristic function being selected to compensate for aberration in the eye when the optical element is located near the cornea.

In some embodiments, the optical medium has a characteristic function selected to reduce astigmatism.

In some embodiments, the optical element is weighted.

In one aspect, the invention features a method including implanting a first magnet at a first location in an eye of a patient, implanting a second magnet at a second location in an eye of a patient, and placing an optical element having third and fourth magnets on a cornea of the eye, the third and fourth magnets being disposed such that when the third magnet is aligned with the first magnet, the second magnet is aligned with the fourth magnet.

In some embodiments, the method includes measuring aberration in the eye when the optical element is placed on the cornea, and on the basis of the measured aberration, shaping the optical element such that a characteristic function associated with refraction therethrough compensates for aberration in the eye when the shaped optical element is placed on the cornea.

As used herein, a "visual axis" means any line passing through the pupil of an eye and passing through any portion of the retina.

As used herein, a "characteristic function" means a function such as a point characteristic, an angle characteristic, or a mixed characteristic that describes refraction of a wavefront of light through a medium.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will become apparent from the following description, and from the claims.

DESCRIPTION

Figure 1A:
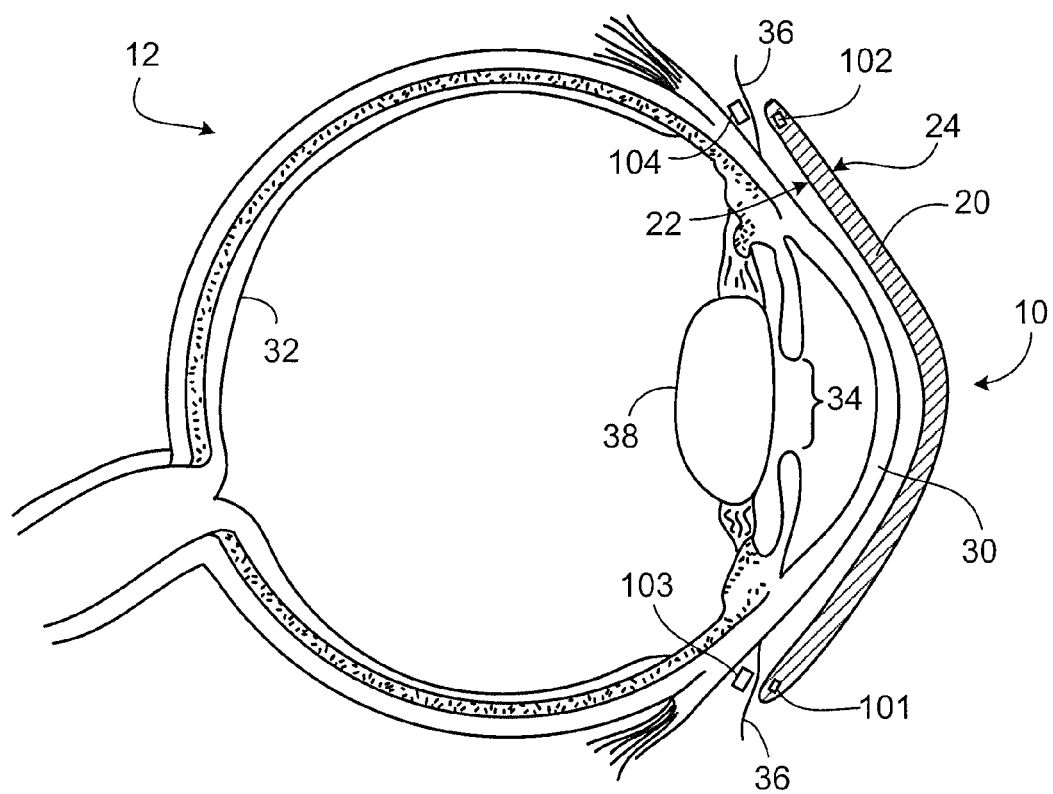
FIG. 1A-C are side views of a vision prosthesis on the eye of a patient.

FIG. 1A shows a vision prosthesis 10 on an eye 12 of a patient. The vision prosthesis 10 includes an optical element 20 having a back surface 22 that is shaped to be positioned near the cornea 30 of a patient's eye 12. The optical element 20 may contact the cornea 30. However, the optical element is positioned to allow fluid (e.g., tears) to flow between the optical element 20 and the cornea. The optical element 20 is optically transparent (or partially transparent) with a front surface 24 that is shaped to provide visual correction as described in more detail below. The optical element 20 can be in the form of a contact lens (e.g., a hard contact lens, a soft contact lens, a "gas permeable" contact lens, etc.).

The optical element 20 includes a first magnet 101 embedded at a location selected to avoid intersection of the first magnet 101 with a visual axis of the eye 12 (e.g., at the periphery of the optical element 20). Optionally, the optical element 20 includes a second magnet 102 embedded at a location selected to avoid intersection of the second magnet 102 with a visual axis of the eye 12. Because they are at a location selected to avoid intersection with a visual axis of the eye 12, the magnets 101-102 do not interfere with an image formed on the retina 32 from light entering the pupil 34.

Third and fourth magnets 103-104 are implanted in the eye 12 of the patient at locations corresponding to the first and second magnets 101-102 in the optical element 20. The third magnet 103 is located in the conjunctiva 36 proximal to the first magnet 101, and the fourth magnet 104 is located in the conjunctiva 36 proximal to the second magnet 102. Alternatively, the third and fourth magnets 103-104 can be implanted in another location in the eye 12. For example, in an embodiment shown in FIG. 1B, the third and fourth magnets 103-104 are implanted within the cornea 30. When the optical element 20 only includes one magnet 101, only one magnet 103 is implanted in the eye 12, as shown in FIG. 1C.

Figure 1B:
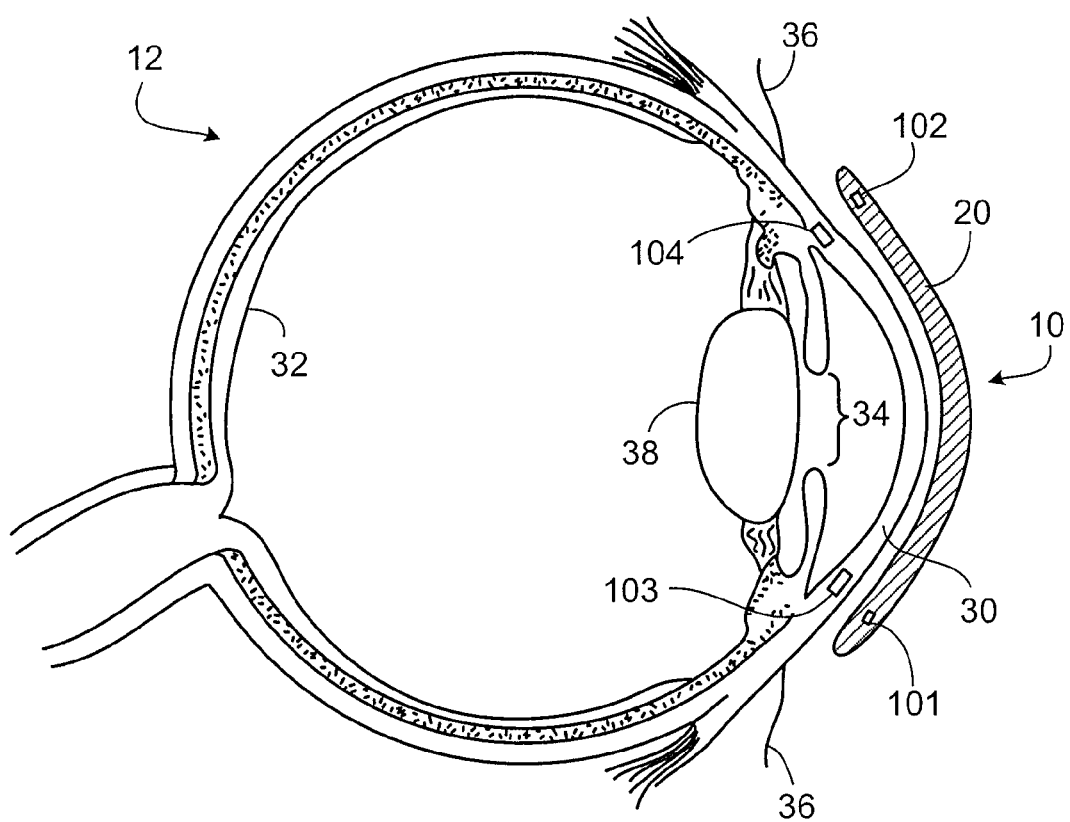
Figure 1C:
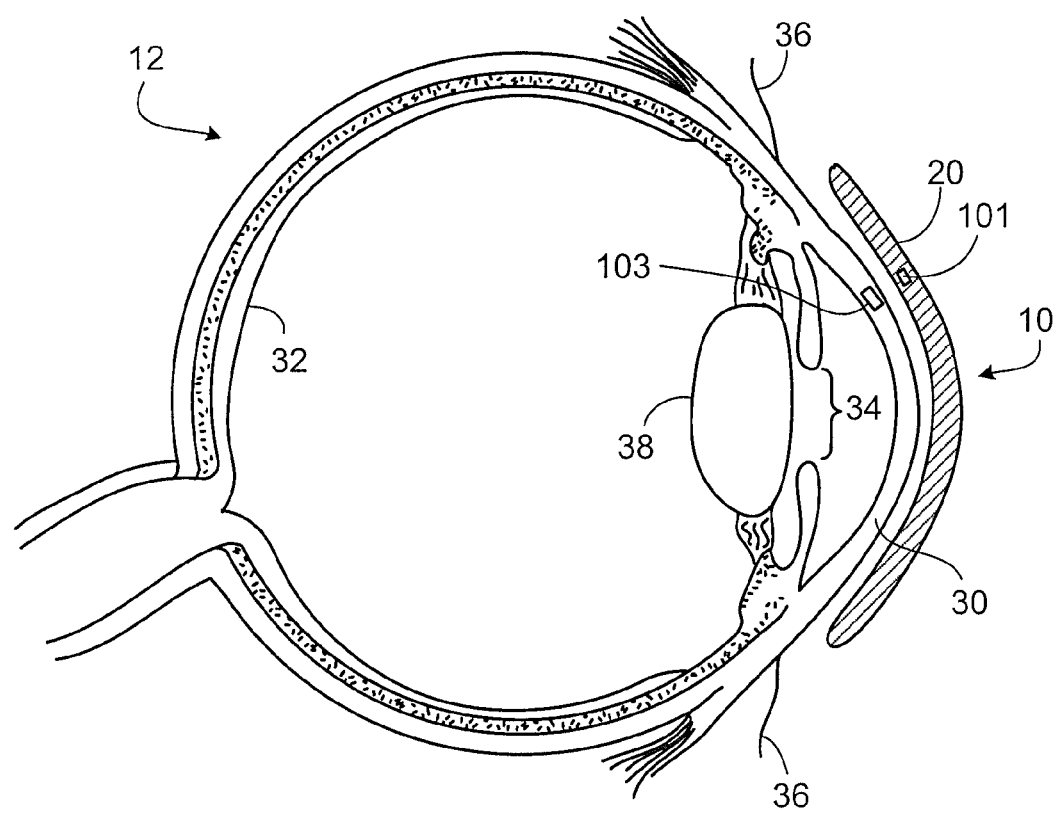

When the optical element 20 is placed over the cornea 30, as shown in FIGS. 1A-B, the proximal sides of the first and third magnets 101, 103 are of opposite polarity, and the proximal sides of the second and fourth magnets 102, 104 are of opposite polarity. The first and third magnets 101, 103 are secured near each other due to magnetic attraction. Similarly, the second and fourth magnets 102, 104 are secured near each other due to magnetic attraction. This pairing of magnets secures the location and orientation of the optical element 20 with respect to the eye 12.

The first and second magnets 101-102 can be located in any of a variety of locations on the periphery of the optical element 20. Some of the possible locations are illustrated in FIGS. 2A-D. In one example (FIG. 2A), the first and second magnets 101-102 are symmetrically located on opposite sides (0° and 180°) of the optical element 20. This arrangement allows secure placement of the optical element 20 in two possible orientations. In one orientation the first magnet 101 is paired with the third magnet 103, and in the other orientation, the first magnet 101 is paired instead with the fourth magnet 104.

Figure 2A:
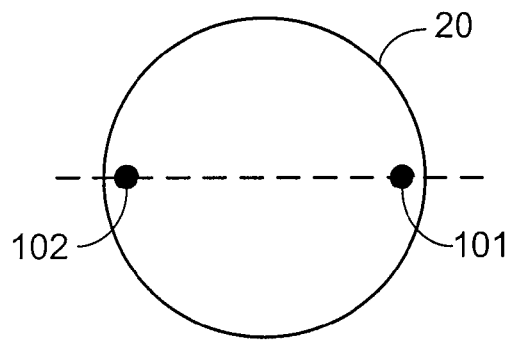
FIG. 2A-D, and F are front views of a vision prosthesis.
Figure 2B:
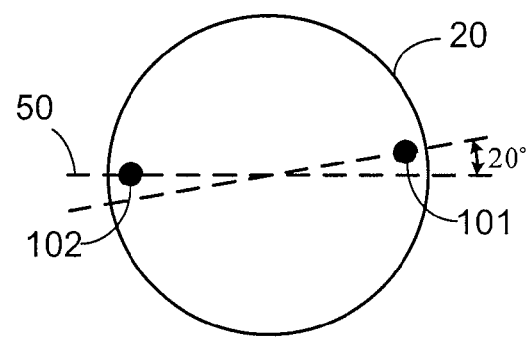
Figure 2C:
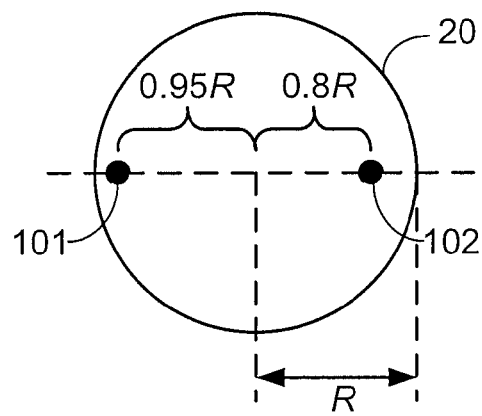
Figure 2D:
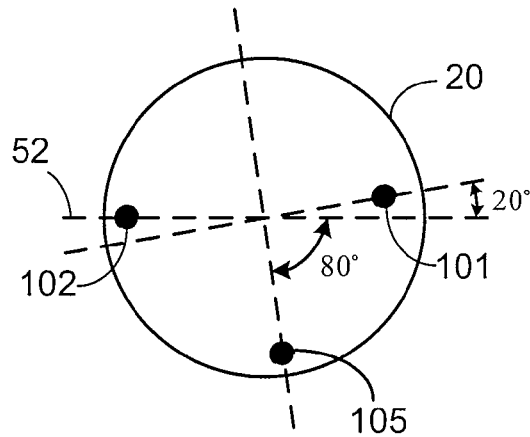
Figure 2E:
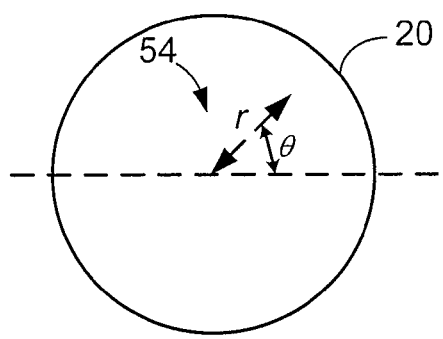
FIG. 2E shows a polar coordinate system with respect to a vision prosthesis.

A single secure orientation can be obtained by arranging the first magnet 101 in an asymmetric position with respect to the second magnet 102. In one example of an asymmetric arrangement (FIG. 2B), the first magnet 101 is at a location 20° relative to an axis 50 and the second magnet 102 is at a location corresponding to 180° relative to that axis 50. In another example of an asymmetric arrangement (FIG. 2C), the first magnet 101 is at a radial location corresponding to 0.95 R and the second magnet 102 is at a radial location corresponding to 0.8 R, where R is the radius of the optical element 20. The optical element 20 can also have an asymmetric arrangement of more than two magnets, as shown in FIG. 2D, with a first magnet 101 at 20°, a second magnet 102 at 180°, and a third magnet 105 at −80°, relative to an axis 52. In general, an asymmetric arrangement of two magnets is one in which $r_1 \neq r_2$ or $\theta_1 \neq \theta_2 + 180°$ where $r_1$ and $\theta_1$ are polar coordinates of the center of the first magnet 101, and $r_2$ and $\theta_2$ are polar coordinates of the center of the second magnet 102, with respect to a polar coordinate system 54 at the center of the optical element (FIG. 2E).

Figure 2F:
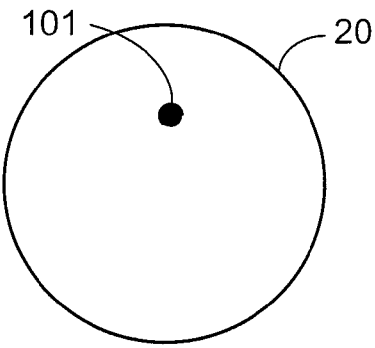

In an alternative embodiment, the optical element 20 includes only a first magnet 101 as shown in FIG. 2F. For example, when the optical element 20 is shaped so that the primary movement of the optical element 20 with respect to the cornea 30 is rotation, only a single magnet is used to fix the orientation of the optical element 20 with respect to the cornea 30.

In another alternative embodiment, the vision prosthesis 10 includes a magnetic element in the form of magnetic particles that are embedded in the optical element 20. Since magnetic particles can be embedded in an optically transparent material to form a transparent magnetic material, such magnetic particles need not be located to avoid intersection with a visual axis of the eye 12. For example, a transparent magnetic material can include a magnetic aerogel or a magnetic composite aerogel such as one of the magnetic silica composite aerogels described in the reference *High-coercivity ultralight transparent magnets* (Applied Physics Letters, Volume 82, pages 4307-4309), the contents of which are herein incorporated by reference. In this embodiment, the magnetic material is distributed throughout the optical element so that the spatial distribution of magnetization is asymmetric with respect to a polar coordinate system as described above with reference to FIG. 2E. A single secure orientation of the optical element 20 is obtained by positioning one or more magnets in the eye in locations corresponding to the spatial distribution of magnetization in the optical element 20.

In the examples described herein, the magnets 101-104 can be disk magnets composed of a ferromagnetic material. The third and fourth magnets 103-104 can be coated with a biocompatible material such as acrylic to make the magnets more suitable for implantation in the eye (e.g., to reduce irritation of structures of the eye or toxicity of material in the eye). Alternatively, any of the magnets 101-104 can be another type of magnet, such as an electromagnet (e.g., a current carrying coil). An electromagnet can be turned on or off or adjusted in magnetic strength by controlling a current that is supplied to the electromagnet by a power source (e.g., implanted in the eye or embedded in the optical element 20).

Figure 3:
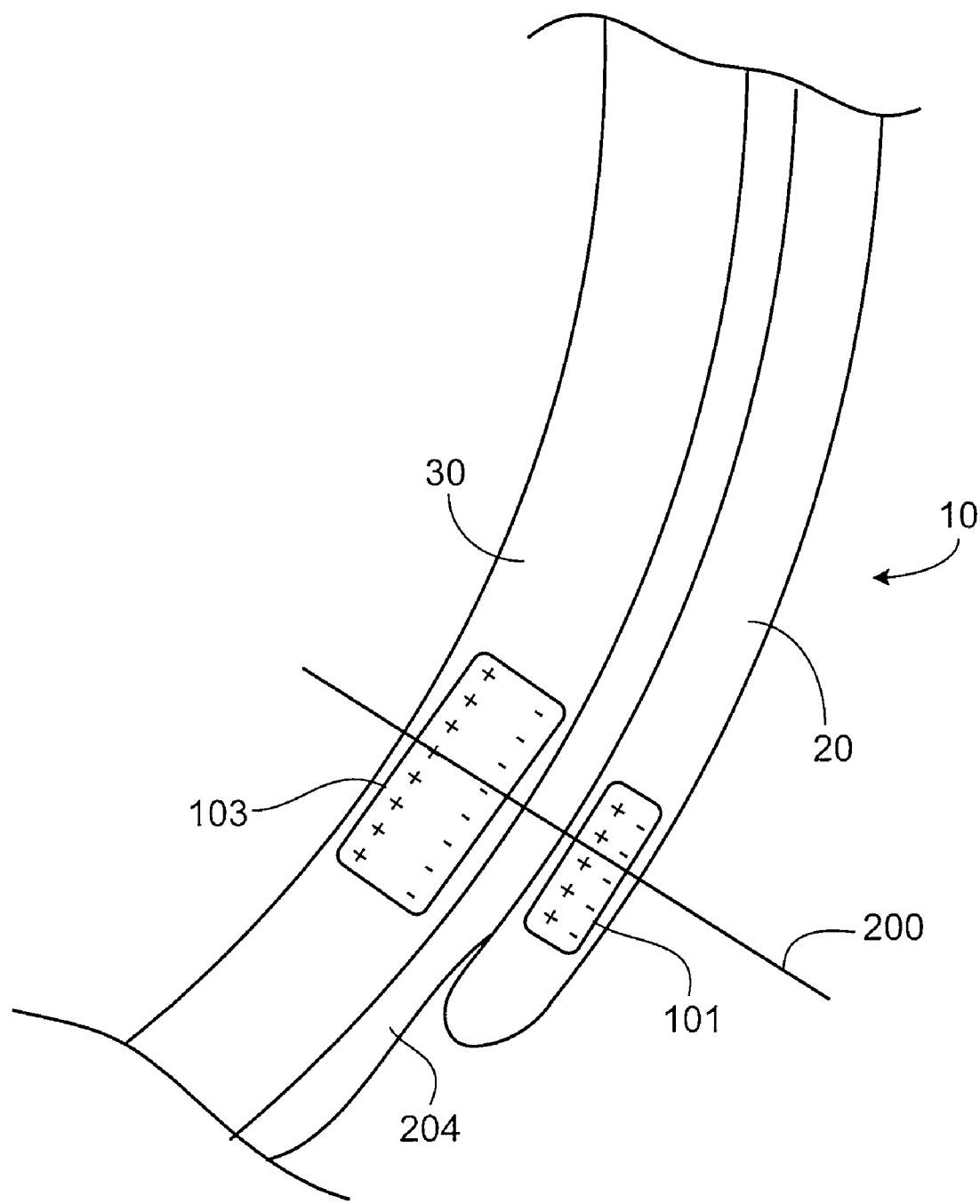
FIG. 3 is a close-up view of a portion of a vision prosthesis on the eye of a patient.

Referring to FIG. 3, the use of magnetic force allows the position and/or orientation of the optical element 20 to be secured is such a way that the optical element 20 is able to temporarily shift from an equilibrium position 200 (in which the centers of the magnets 101 and 103 are aligned) and to return to that equilibrium position 200 within a predetermined tolerance. This movement is useful to allow the exchange of tears 204 under the optical element 20. By using a third magnet 103 that is larger than the first magnet 101 (e.g., having a diameter that is larger by 50%), the optical element 20 will move slightly when the patient blinks, but return to the equilibrium position 200 between blinks. Alternatively, the first magnet 101 could be larger than the third magnet 103. Even though there is a single equilibrium position 200, allowing for more movement due to a blink may also allow a larger shift from the equilibrium position 200 due to stresses exerted on the optical element 20 by the eye. The amount of movement due to a blink and the maximum excursion the optical element 20 can undergo and still return to the same equilibrium position 200 can be tuned (e.g., by changing the ratio of the sizes of the paired magnets, or by purposefully misaligning the paired magnets in the equilibrium position 200) to meet desired movement and/or error criteria. The magnetic techniques described herein can be used alone or in combination with other techniques such as using a truncated, ballasted, or otherwise "weighted" optical element 20. For example, a weighted optical element 20 can be thicker on a lower portion outside of an optical axis (e.g., a lower rim), such that gravity tends to orient the optical element 20 when a patient is upright.

The secure position and/or orientation of the optical element 20 with respect to the eye 12 is useful for various types of visual correction in which aberrations are caused by asymmetric features. Asymmetric features are those topographic features on the cornea or lens that change with circumferential angle, as opposed to only changing with radius. A surface of the optical element 20 can be shaped to correct for wavefront aberrations due to such features in a patient's cornea 30 or natural crystalline lens 38. For example, a surface of the optical element 20 can have an "asymmetric shape" defined by $f(r,\theta) \neq f(r,-\theta)$, where $f(r,\theta)$ is a height of a surface. The magnets 101-104 will then assure that the optical element 20 remains correctly oriented relative to the asymmetric features.

A wavefront of light passing through the optical element 20 will be altered in a way that can be described by a characteristic function associated with refraction through the optical element 20. The characteristic function of an optical element can be estimated from knowledge of the optical path length traversed by any ray of light passing through any portion of the element. For an optical element composed of one or more types of media having various surfaces, the optical path length can be determined from the index of refraction within the media and the shapes of the surfaces. This type of analysis can also be used to design and construct an optical element having a desired characteristic function.

By measuring any pre-existing aberrations in the patient's eye 12 (e.g., using an aberrometer), the optical element 20 can be designed to have a characteristic function that cancels the effects of pre-existing aberrations. As a result, an optical element 20 placed on the cornea 30 reduces pre-existing aberrations.

Before measuring the pre-existing aberrations, the third and fourth magnets 103-104 are implanted in the patient's eye 12. The pre-existing aberrations are measured with a "blank" optical element 20 on the cornea 30. The blank optical element 20 has the first and second magnets 101-102, and an optical element 20 that has a uniform thickness. The front surface 24 of the optical element 20 (and hence its thickness) is then shaped based on the resulting measurement of pre-existing aberrations. This shaping can be performed, for example, by laser ablation using an excimer laser on an optical element 20 composed of a material such as polymethyl methacrylate (PMMA) or acrylic. Alternatively, the front surface 24 of the optical element 20 can be etched to the desired shape using mechanical or photochemical etching.

Some wavefront aberration due to irregularities in the shape of the cornea 30 (e.g., astigmatism) can be partially corrected with a hard contact lens having a smooth and symmetric shape. A soft contact lens, however, generally conforms to the cornea 30. Consequently, the surface of the soft contact lens is likely to have irregularities that cause wavefront aberration. Using the techniques described above, the thickness of a soft contact lens can be varied to compensate for the irregularities in the cornea 30. This will cause the outer surface of the soft contact lens (the surface that first refracts an incoming ray of light) to be smooth and symmetric when the contact lens is on the eye. Either hard or soft contact lenses can be shaped as described above to compensate for higher order wavefront aberrations (e.g., higher order than astigmatism) and/or irregularities in other structures of the eye, such as the natural crystalline lens.

Figure 4:
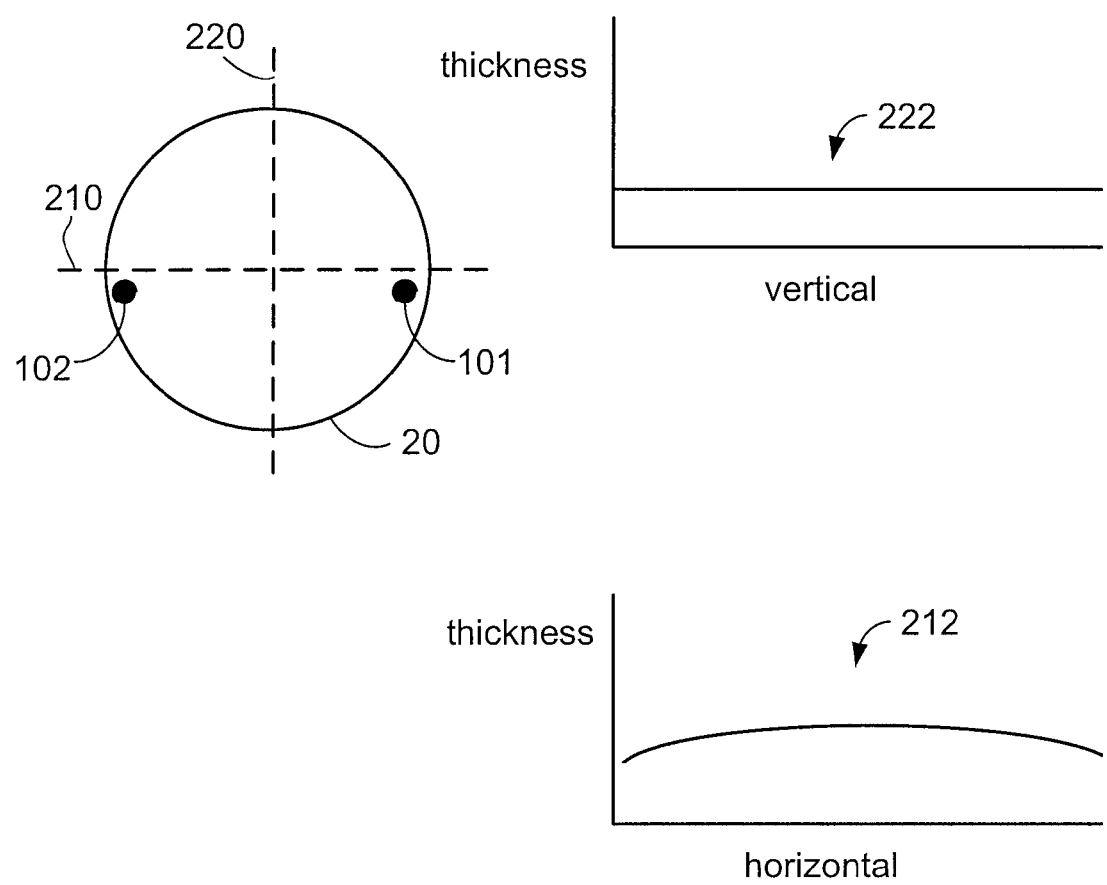
FIG. 4 is a vision prosthesis with a cylindrically shaped optical element.

In some embodiments, including those discussed in connection with FIGS. 2B-D, the vision prosthesis 10 uses an arrangement of magnets to achieve a single preferred orientation of the optical element 20 with respect to the eye 12. Other embodiments can have two or more equivalent preferred orientations. Referring to FIG. 4, one embodiment includes an optical element 20 having a cylindrical shape, for example, to correct for astigmatism in a patient's eye. In this embodiment, the horizontal cross-section 210 has a curved profile 212, and the vertical cross-section 220 has a uniform profile 222. Such a "cylindrical contact lens" has two equivalent preferred orientations. The cylindrical contact lens is thus compatible with both an asymmetric arrangement of magnets, such as those in FIGS. 2B-2D, and the symmetric arrangement of FIG. 2A.

For a patient with an eye having both defocus (i.e., myopia or hyperopia) and astigmatism, two orthogonal profiles of an optical element can have similar circular profiles (to correct defocus) with a slight difference in their radii of curvature (to correct astigmatism). Similarly, the shape of an optical element 20 selected to offset an "aberration map" of a patient's eye can include symmetric defocus corrections as well as asymmetric low or high order aberration corrections.

Figure 5:
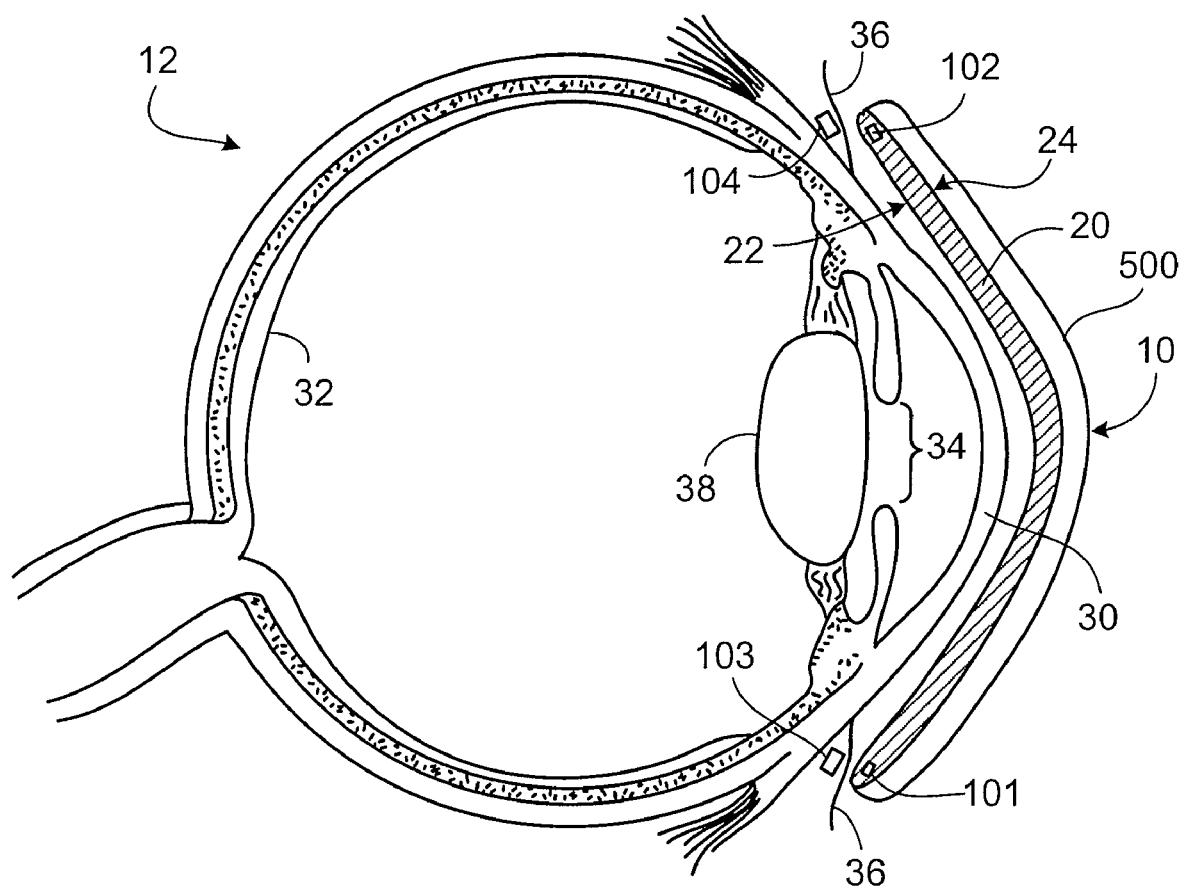
FIG. 5 is a vision prostheses included as part of an imaging system.

In some embodiments, the vision prosthesis 10 is part of an imaging system 500 (FIG. 5) that also provides functions such as focusing (or "accommodation") and/or adaptive optics wavefront correction. In such cases, the optical element 20 can have a shape or index of refraction that changes in response to a stimulus (e.g., an infrared beam). Power can be supplied to the system from an annular photoelectric cell attached to, or separate from the vision prosthesis 10. Portions of such an imaging system can be implanted inside the eye (e.g, in the lens bag or in the anterior or posterior chamber). An imaging system of this type is described fully in U.S. Pat. No. 6,638,304, the contents of which are herein incorporated by reference. Instead of having a varying thickness to correct for aberrations, the optical element 20 can have a uniform thickness and include portions of an imaging system. For example, the optical element 20 can include an electro-optic component of a adaptive optics system for which it is useful to have a secured position and/or orientation with respect to the eye.

It is to be understood that while the invention has been described in conjunction with the detailed description thereof, the foregoing description is intended to illustrate and not limit the scope of the invention, which is defined by the scope of the appended claims.

What is claimed is:

1. A vision prosthesis comprising:
   an aberration correcting optical element having a surface that is shaped to a cornea of an eye, wherein the optical element comprises an optical medium having a characteristic function associated with refraction therethrough, the optical medium being configured such that the characteristic function compensates for aberration in the eye when the optical element is located near the cornea;

a magnetic element embedded in the optical element, wherein the magnetic element comprises a first magnet at a first location on the optical element, the first location being selected to avoid intersection of the first magnet with a visual axis of the eye;

a second magnet adapted to be implanted within the eye, the second magnet being disposed such that when the optical element is located over the cornea the second magnet is proximate to and aligned with the first magnet, wherein the second magnet is adapted to be implanted at a location in the eye selected from the group consisting of: within the conjunctiva of the eye; under the conjunctiva of the eye; within the cornea of the eye; and under the cornea of the eye; and wherein the optical element comprises a contact lens.

2. The vision prosthesis of claim 1, further comprising:

a third magnet at a second location on the optical element, the second location being selected to avoid intersection of the third magnet with a visual axis of the eye.

3. The vision prosthesis of claim 2, further comprising:

a fourth magnet adapted to be implanted within the eye, the second and fourth magnets being disposed such that when the optical element is located over the cornea the second magnet is aligned with the first magnet, and the third magnet is aligned with the fourth magnet.

4. The vision prosthesis of claim 2, wherein the third magnet is at an asymmetric location with respect to the first magnet.

5. The vision prosthesis of claim 1, wherein the first and second magnets have different sizes.

6. The vision prosthesis of claim 5, wherein the second magnet is larger than the first magnet.

7. The vision prosthesis of claim 1, wherein the first magnet is selected from the group consisting of a ferromagnetic material and an electromagnet.

8. The vision prosthesis of claim 1, wherein the second magnet is selected from the group consisting of a ferromagnetic material and an electromagnet.

9. The vision prosthesis of claim 1, wherein the contact lens comprises a hard contact lens.

10. The vision prosthesis of claim 1, wherein the contact lens comprises a soft contact lens.

11. The vision prosthesis of claim 1, wherein the contact lens has a surface having an asymmetric shape.

12. The vision prosthesis of claim 1, further comprising a portion of an imaging system attached to the optical element.

13. The vision prosthesis of claim 1, wherein the optical medium has a characteristic function selected to reduce a stigmatism.

14. The vision prosthesis of claim 1, wherein the optical element is weighted.

15. The vision prosthesis of claim 1, wherein the optical medium is configured such that the characteristic function compensates for aberration in the eye and compensates for defocus in the eye when the optical element is located near the cornea.

16. The vision prosthesis of claim 1, wherein the optical medium is configured such that the characteristic function compensates for aberration in the eye without compensating for defocus in the eye when the optical element is located near the cornea.

* * * * *

UNITED STATES PATENT AND TRADEMARK OFFICE
CERTIFICATE OF CORRECTION

| | | |
|---|---|---|
| PATENT NO. | : 7,753,952 B2 | Page 1 of 1 |
| APPLICATION NO. | : 12/140678 | |
| DATED | : July 13, 2010 | |
| INVENTOR(S) | : Dimitri T. Azar | |

It is certified that error appears in the above-identified patent and that said Letters Patent is hereby corrected as shown below:

Column 6, Line 64, In Claim 1, after "shaped" insert -- to conform --

Signed and Sealed this

Twenty-sixth Day of October, 2010

David J. Kappos
*Director of the United States Patent and Trademark Office*